(12) United States Patent
Black et al.

(10) Patent No.: US 10,180,393 B2
(45) Date of Patent: Jan. 15, 2019

(54) SAMPLE CELL (71) Applicant: CASCADE TECHNOLOGIES HOLDINGS LIMITED, Stirling (GB)

(72) Inventors: Paul Black, Stirling (GB); Colin Lumsden, Stirling (GB)

(73) Assignee: CASCADE TECHNOLOGIES HOLDINGS LIMITED (GB)

( * ) Notice: Subject to any disclaimer, the term of this patent is extended or adjusted under 35 U.S.C. 154(b) by 0 days.

(21) Appl. No.: 15/133,517

(22) Filed: Apr. 20, 2016

(65) Prior Publication Data

US 2017/0307519 A1    Oct. 26, 2017

(51) Int. Cl.
| | | |
|---|---|---|
| *G01N 21/31* | (2006.01) | |
| *G01N 21/01* | (2006.01) | |
| *G01N 33/00* | (2006.01) | |
| *G01N 21/03* | (2006.01) | |
| G01N 21/3504 | (2014.01) | |

(52) U.S. Cl.
CPC .......... *G01N 21/3103* (2013.01); *G01N 21/01* (2013.01); *G01N 21/031* (2013.01); *G01N 33/0036* (2013.01); *G01N 21/3504* (2013.01); *G01N 2021/3125* (2013.01); *G01N 2201/0668* (2013.01); *G01N 2201/06113* (2013.01); *G01N 2201/06146* (2013.01)

(58) Field of Classification Search
CPC .... G01N 21/255; G01N 21/39; G01N 21/031; G01N 2201/0221; G01N 2021/399; G01N 2201/0668; G01N 33/0036; G01N 21/3103; G01N 21/01; G01N 2201/06113; G01N 2201/06146; G01N 2021/3125
See application file for complete search history.

(56) References Cited

U.S. PATENT DOCUMENTS

| | | | |
|---|---|---|---|
| 2,844,730 A | | 7/1958 | Tandler et al. |
| 3,792,272 A | * | 2/1974 | Harte ................ G01N 21/3504 |
| | | | 250/338.1 |
| 3,851,213 A | | 11/1974 | Van Dam et al. |
| 4,598,201 A | | 7/1986 | Fertig et al. |
| 4,927,265 A | | 5/1990 | Brownlee |
| 5,407,638 A | | 4/1995 | Wang |

(Continued)

FOREIGN PATENT DOCUMENTS

| | | |
|---|---|---|
| CN | 104155241 | 11/2014 |
| DE | 19716061 | 3/1998 |

(Continued)

OTHER PUBLICATIONS

Official Action for U.S. Appl. No. 15/132,993, dated May 5, 2018 17 pages.

(Continued)

*Primary Examiner* — Sang Nguyen
(74) *Attorney, Agent, or Firm* — Sheridan Ross P.C.

(57) ABSTRACT

An optical cell comprises first and second opposed reflecting elements, an entrance aperture in the first reflecting element and an exit aperture in the second reflecting element, wherein the entrance and exit apertures are configured such that, in operation, light introduced into the cell via the entrance aperture is reflected at least once by the second reflecting element and at least once by the first reflecting element before leaving the cell via the exit aperture.

16 Claims, 5 Drawing Sheets

(56) References Cited

U.S. PATENT DOCUMENTS

| | | | | |
|---|---|---|---|---|
| 5,625,189 | A | * | 4/1997 | McCaul ............... G01N 21/274 250/341.1 |
| 5,760,895 | A | | 6/1998 | Kebabian |
| 6,545,278 | B1 | | 4/2003 | Mottier et al. |
| 6,657,198 | B1 | | 12/2003 | May |
| 7,590,156 | B1 | * | 9/2009 | Richardson ........... H01S 3/1118 372/11 |
| 7,800,751 | B1 | * | 9/2010 | Silver ................. G01N 21/031 356/246 |
| 8,269,971 | B1 | | 9/2012 | Marsh et al. |
| 2003/0071218 | A1 | | 4/2003 | Nakamura et al. |
| 2006/0119851 | A1 | * | 6/2006 | Bounaix ............... G01N 21/031 356/437 |
| 2007/0082407 | A1 | | 4/2007 | Little |
| 2007/0230520 | A1 | | 10/2007 | Mordaunt et al. |
| 2008/0135760 | A1 | | 6/2008 | May |
| 2010/0195096 | A1 | | 8/2010 | Schlezinger |
| 2010/0228688 | A1 | | 9/2010 | Little et al. |
| 2010/0284017 | A1 | * | 11/2010 | Reyes ................... G01J 3/4535 356/452 |
| 2011/0176068 | A1 | | 7/2011 | Miller |
| 2012/0037326 | A1 | | 2/2012 | Ublacker |
| 2012/0182555 | A1 | | 7/2012 | Statz et al. |
| 2013/0319110 | A1 | | 12/2013 | Otera |
| 2014/0077083 | A1 | | 3/2014 | Birnkrant et al. |
| 2014/0204382 | A1 | * | 7/2014 | Christensen ........... G01N 21/39 356/402 |
| 2015/0138533 | A1 | | 5/2015 | Bolles et al. |
| 2015/0177131 | A1 | | 6/2015 | Liu et al. |
| 2015/0241339 | A1 | | 8/2015 | Maksyutenko et al. |
| 2015/0285679 | A1 | | 10/2015 | Kasiutsich et al. |
| 2016/0084710 | A1 | | 3/2016 | Keller et al. |
| 2016/0170218 | A1 | | 6/2016 | Johnson et al. |

FOREIGN PATENT DOCUMENTS

| | | |
|---|---|---|
| DE | 102005032722 | 10/2006 |
| DE | 102007038943 | 2/2009 |
| EP | 0768523 | 4/1997 |
| EP | 0896216 | 2/1999 |
| EP | 0994340 | 4/2000 |
| EP | 1193488 | 4/2002 |
| EP | 1605251 | 12/2005 |
| EP | 1734347 | 12/2006 |
| EP | 1783481 | 5/2007 |
| EP | 1836479 | 9/2007 |
| EP | 1972922 | 9/2008 |
| EP | 2375237 | 10/2011 |
| EP | 2607891 | 6/2013 |
| EP | 2927668 | 10/2015 |
| EP | 2344862 | 2/2016 |
| EP | 2993461 | 3/2016 |
| FR | 2735236 | 12/1996 |
| FR | 2971587 | 8/2012 |
| FR | 3009655 | 2/2015 |
| GB | 2389177 | 12/2003 |
| GB | 2391310 | 2/2004 |
| GB | 2401679 | 11/2004 |
| GB | 2493833 | 2/2013 |
| GB | 2497295 | 6/2013 |
| WO | WO 95/26497 | 10/1995 |
| WO | WO 00/73768 | 12/2000 |
| WO | WO 03/046522 | 6/2003 |
| WO | WO 2004/023114 | 3/2004 |
| WO | WO 2004/113169 | 12/2004 |
| WO | WO 2006/022550 | 3/2006 |
| WO | WO 2006/029920 | 3/2006 |
| WO | WO 2006/061681 | 6/2006 |
| WO | WO 2006/127722 | 11/2006 |
| WO | WO 2008/048994 | 4/2008 |
| WO | WO 2008/079032 | 7/2008 |
| WO | WO 2009/052157 | 4/2009 |
| WO | WO 2009/105571 | 8/2009 |
| WO | WO 2009/155459 | 12/2009 |
| WO | WO 2010/024756 | 3/2010 |
| WO | WO 2012/050696 | 4/2012 |
| WO | WO 2012/093952 | 7/2012 |
| WO | WO 2012/151358 | 11/2012 |
| WO | WO 2012/151678 | 11/2012 |
| WO | WO 2013/188914 | 12/2013 |
| WO | WO 2014/033465 | 3/2014 |
| WO | WO 2014/162536 | 10/2014 |
| WO | WO 2015/33582 | 3/2017 |

OTHER PUBLICATIONS

Official Action for U.S. Appl. No. 15/132,993, dated Nov. 24, 2017 15 pages.

International Search Report and Written Opinion for International (PCT) Patent Application No. PCT/GB2017/051068, dated Jun. 20, 2017, 14 pages.

International Search Report and Written Opinion for International (PCT) Patent Application No. PCT/GB2017/051078, dated Jul. 12, 2017, 16 pages.

* cited by examiner

SAMPLE CELL

INTRODUCTION

The present invention relates to a sample cell, for example a sample cell for use in gas analysis based on laser absorption spectroscopy.

BACKGROUND

Known gas analysis systems also include one or more sample cells, for example one or more Herriot cells, for containing a gas sample to be analysed and through which a laser beam passes in order to interact with the gas sample. Arrangement of sample cells and other optical components affects the geometry, size and performance of a gas analysis system. In order for instance to make a system compact, for example to be able to contain the system within a compact, transportable housing, it can be important to provide a suitable arrangement of the sample cell and other optical components.

SUMMARY

In a first aspect of the invention, there is provided an optical cell comprising: first and second opposed reflecting elements; an entrance aperture in the first reflecting element; and an exit aperture in the second reflecting element. The entrance and exit apertures may be configured such that, in operation, light introduced into the cell via the entrance aperture is reflected at least once by the second reflecting element and at least once by the first reflecting element before leaving the cell via the exit aperture.

The light may comprise laser radiation, for example at least one laser beam. The light may comprise infra-red or visible light, for example, infra-red or visible laser beam. The laser beam may comprise a pulsed laser beam comprising pulsed laser radiation. The optical cell may be a multi-pass optical cell.

The optical cell may comprise a Herriot-type cell.

The optical cell may comprise an adapted or modified Herriot cell.

The path followed by the light between the entrance and exit apertures may define a path length, and the cell may comprise an adjustment apparatus for obtaining relative movement of the second reflecting element and the first reflecting element such that the path length of the cell is modified.

The relative movement may comprise keeping one of the first reflecting element and the second reflecting element in a fixed position and moving (for example rotating and/or translating) the other of the first reflecting element and the second reflecting element. Alternatively, the relative movement may comprise may comprise moving (for example rotating and/or translating) both of the first reflecting element and the second reflecting element. The adjustment apparatus may move (for example rotate and/or translate) the first reflecting element and/or the second reflecting element.

The adjustment apparatus may be configured to modify the path length by modifying the number of reflections of the light between entering the cell and exiting the cell.

The path length over which the light interacts with the sample gas in the cell may be modified by altering the number of reflections of the light by the first reflecting element and the second reflecting element before the light exits the cell.

The relative movement may comprise a rotation of the second reflecting element and/or the first reflecting element.

The relative movement may comprise a translation of the second reflecting element and/or the first reflecting element.

In operation said light may reflect from the first reflective element at a plurality of first reflection points and may reflect from the second reflective element at a plurality of second reflection points.

The cell may comprise an adjustment apparatus for obtaining relative movement of the second reflecting element and the first reflecting element thereby to position the exit aperture at a selected one of the second reflection points.

Thus, the number of reflections of the light before exiting the cell may be altered by suitable positioning of the exit aperture.

The adjustment apparatus may be configured to obtain said relative movement such as to step the position of the exit aperture from one of the second reflection points to a further, selected one of the second reflection points.

The adjustment apparatus may be configured to cause relative movement of the exit aperture and the second reflection points by predetermined amounts that correspond to the separations of the second reflection points.

At least some, optionally each, of the plurality of first reflection points may be arranged at substantially the same radial distance from an axis of the first reflecting element. At least some, optionally each, of the plurality of second reflection points may be arranged at substantially the same radial distance from an axis of the second reflecting element.

At least some, optionally each, of the plurality of first reflection points may be spaced from a respective neighbouring one of the plurality of first reflection points by substantially the same first angle. At least some, optionally each, of the plurality of first reflection points may be spaced from a respective neighbouring one of the plurality of second reflection points by substantially the same second angle.

The first angle may be substantially the same as the second angle.

The entrance aperture may be located at an off-axis position with respect to a central axis of the first reflecting element. The exit aperture may be located at an off-axis position with respect to a central axis of the second reflecting element.

The first reflecting element may have a reflecting surface that is circularly symmetric. The second reflecting element may have a reflecting surface that is circularly symmetric.

The first reflecting element may comprise a paraboloid mirror. The second reflecting element may comprise a paraboloid mirror.

In a further aspect of the invention, which may be provided independently, there is provided a detection system comprising: at least one laser configured to produce at least one laser beam for excitation of one or more different compounds; a sample cell for containing a volume of sample gas; at least one directing device configured to direct the at least one laser beam to the sample cell; and a detector apparatus for detecting light output from the cell, wherein the sample cell comprises: first and second opposed reflecting elements; an entrance aperture in the first reflecting element; and an exit aperture in the second reflecting element, wherein the entrance and exit apertures are configured such that, in operation, light introduced into the cell via the entrance aperture is reflected at least once by the second reflecting element and at least once by the first reflecting element before leaving the cell via the exit aperture.

The detector apparatus may be arranged at a first side of the sample cell and the at least one laser may be arranged at a second, substantially opposite side of the sample cell.

The system may be a continuous emission monitoring system.

The at least one compound may comprise at least one of: NO, $NO_2$, $H_2O$, CO, $CO_2$, $CH_4$, $SO_2$, $NH_3$, $C_2H_2$ and $O_2$.

In a further aspect of the invention, which may be provided independently, there is provided a method of testing, measuring or detecting the presence of a gas comprising: directing light into a sample cell containing the gas via an entrance aperture in a first reflecting element of the sample cell; receiving the light from an exit aperture in a second reflecting element of the sample cell following reflection of the light between the first and second reflecting elements; and detecting the received light.

Features in one aspect may be applied as features in another aspect in any appropriate combination. For example, any one of method, system or cell features may be applied as any one other of method, system or cell features.

BRIEF DESCRIPTION OF THE DRAWINGS

Various aspects of the invention will now be described by way of example only and with reference to the accompanying drawings, of which.

DETAILED DESCRIPTION OF THE DRAWINGS

Figure 1:
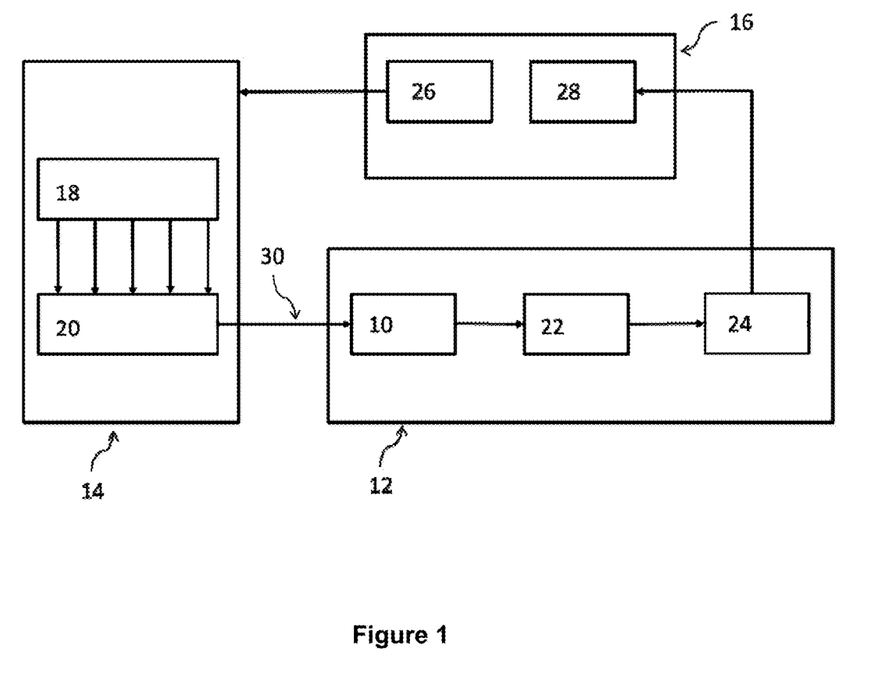
FIG. 1 is a schematic representation of a laser spectroscopy system.

FIG. 1 is a schematic representation of a laser spectroscopy system for analysing gas collected in a sample cell 10 of a sensor apparatus 12. The system comprises a laser module 14 that is optically coupled to the sensor apparatus 12. The system also includes a controller 16 that is electronically, electrically or otherwise connected to the laser module 14 and the sensor apparatus 12. The laser module 14 comprises a plurality of lasers 18 and at least one directing device in the form of a plurality of optical components 20 arranged to direct laser beams from the lasers along a common optical path into the sample cell 10, as described in more detail below in relation to FIG. 2.

In addition to the sample cell 10, the sensor apparatus 12 also includes steering optical components 22 and a detector apparatus 24 comprising a plurality of detectors. The detectors are configured to detect light from the sample cell. The light may be infra-red or visible light or light of any other suitable wavelength or from any suitable part of the electromagnetic spectrum. The controller 16 comprises a control module 26 and a signal processor 28. The control module 26 is configured to control operation of the lasers and the signal processor 28 is configured to process signals obtained from the detector apparatus 24. The controller 16 may be, for example, in the form of a suitably programmed PC or other computer, or may comprise dedicated circuitry or other hardware, for example one or more ASICs or FPGAs or any suitable mixture of hardware and software. The control module 26 and processing module may be provided as separate, distinct components in some embodiments, for example separate processing resources, rather than being provided within the same controller component as shown in FIG. 1.

The sample cell 10 has an optical entrance aperture and an optical exit aperture. The sample cell 10 may, for example, be a Herriot cell or any other suitable type of sample cell. The sample cell 10 of FIG. 1 defines a volume into which a sample of gas can be introduced and collected. The gas can comprise one or more different compounds of interest. An indication of the presence of these compounds in the gas collected in the sample cell 10 can be determined by passing light from the lasers 18 through the sample cell 10. If the light is in a wavelength range that corresponds to the absorption spectrum or absorption lines of the compound of interest, then any absorption of light as it passes through the cell may be due to the presence of the compound of interest in the sample. The level of absorption, once determined, can be used to determine a physical property of the compound of interest in the sample, for example, concentration. As different compounds have absorption spectra at different wavelength, different wavelengths of light are provided to the sample cell 10.

Figure 2:
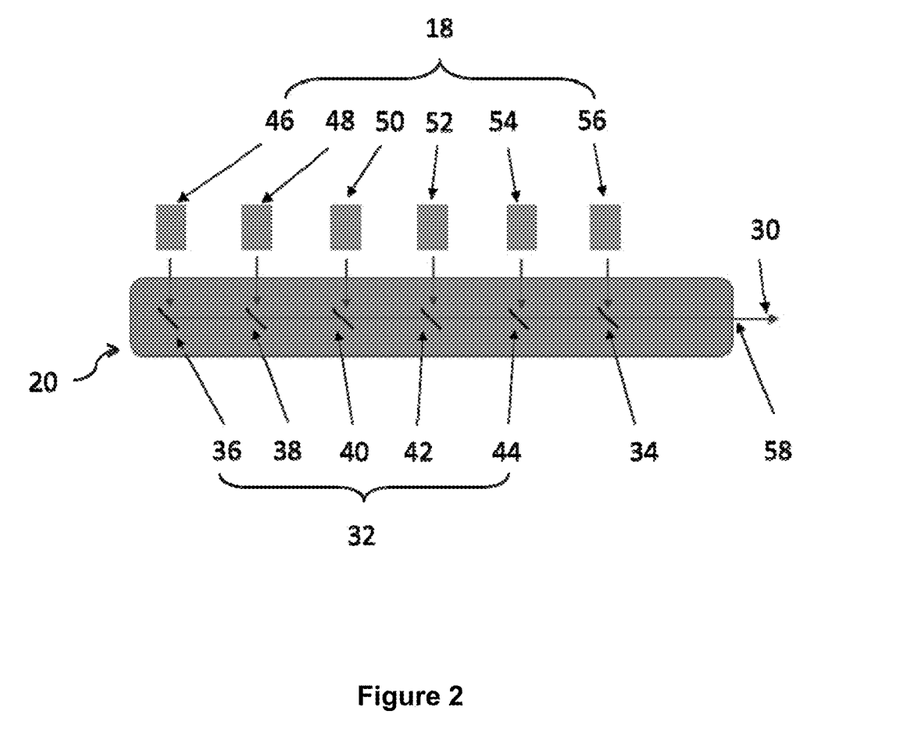
FIG. 2 is a schematic view of a laser module of the laser spectroscopy system.

FIG. 2 is a more detailed schematic view of a part of the laser module 14 of the laser spectroscopy system shown in FIG. 1. The optical components 20 comprise a set of partially reflective mirrors 32 and a dichroic mirror 34. The partially reflective mirrors 32 comprise a first mirror 36, a second mirror 38, a third mirror 40, a fourth mirror 42 and a fifth mirror 44. The lasers 18 comprise a first laser 46, a second laser 48, a third laser 50, a fourth laser 52, a fifth laser 54 and a sixth laser 56. The partially reflective mirrors 32 and the dichroic mirror 34 are configured to direct laser beams from the lasers 18 along a common optical path to point 58. Additional steering optical components to steer the combined laser beam 30 from point 58 along the common optical path to the sample cell 10 are included in the system but not shown in FIG. 2. Each of the lasers 46, 48, 50, 52, 54, 56 has a corresponding mirror 36, 38, 40, 42, 44, 34. The partially reflective mirrors 32 and the dichroic mirror 34 are arranged in a straight line. Each mirror is tilted with respect to this straight line at a 45 degree angle. The straight line defines a direction of propagation from the first mirror 36 to the dichroic mirror 34 and then to point 58. A combined laser beam 30 propagates along the direction of propagation.

Any suitable partially reflective mirrors may be used. In the embodiment of FIG. 2, each of the partially reflective mirrors comprise coated infrared $BaF_2$ or $CaF_2$ windows that have an optical coating applied to control broadband reflection of the front surface. Any other suitable materials can be used in alternative embodiments. In the embodiment of FIG. 2, two coatings are used, an 80:20 (80% transmission, 20% reflection) and a 50:50 (50% transmission, 50% reflection). This can allow the variety of laser powers to be adjusted to harmonise the output power to a consistent value for each laser (within practical limits). More or fewer coatings can be used in alternative embodiments. The coatings of the partially reflective mirrors of FIG. 2 are designed to be broadband, such that any variation in their response to a change in wavelength, particularly around wavelengths of interest, is reduced or minimised.

Any suitable dichroic mirrors may be used. In the embodiment of FIG. 2, the dichroic mirror comprises a coated infrared BaF2 window that has an optical coating applied to cause light lower than a specified wavelength to be reflected and light higher than said specified wavelength to be transmitted. Any other suitable materials can be used in alternative embodiments. In the embodiment of FIG. 2, the coating is such as to reflect light less than 1 μm in wavelength and to transmit light greater than 1 μm in wavelength.

In other embodiments, other suitable types of mirror or optical devices may be used in place of the partially reflective mirrors and the dichroic mirror. For example, in some embodiments a mirror other than a dichroic mirror or partially reflective mirror may be used at the position of dichroic mirror 34, e.g. at the last mirror position before point 58. Such a mirror may be used at the last position to introduce more power into the cell. This can be possible as or if the last position does not have any additional lasers behind it such that no lasers need to pass through the last position. In alternative embodiments, any suitable number and combination of partially reflective mirrors and dichroic mirrors may be used.

Each of the partially reflective mirrors 32 is configured to partially reflect and partially transmit light incident on it. The reflection and transmission properties of the mirror are chosen to direct laser beams from the lasers 18 along the common optical path. In the embodiment of FIG. 2, each of the partially reflective mirrors 32 reflects 20% of the incident light and transmits 80% of the incident light from the corresponding one of the lasers 18. The partially reflective mirrors 32 may have different reflection and transmission properties in alternative embodiments. The dichroic mirror 34 is defined by a reflection wavelength range and is configured to reflect light that has a wavelength in the reflection wavelength range and transmit light with a wavelength outside the reflection wavelength range. The reflection wavelength range of the dichroic mirror 34 is chosen to correspond to a wavelength range of the sixth laser 56, such that light from the sixth laser 56 is reflected and light from the first to fifth lasers is transmitted. The mirrors are flat or non-wedged optical components. Advantageously this allows the system to operate in an orthogonal fashion. For example, the system has a geometrical arrangement such that the direction of propagation from the first mirror 36 to the dichroic mirror 34 is substantially orthogonal to the laser beams output from the lasers 18.

Another advantage of using flat or non-wedged optical components in embodiments is that the directing of the laser beams to the common optical path may be substantially independent of wavelength, for example such that any distortion effects or other artefacts caused by the optical components may be substantially independent of wavelength. However, the use of mirrors may cause the resulting optical signal to be subject to fringe interference effects. These effects can be reduced by selecting the dimensions, in particular the thickness, of the optical components to control the Free Spectral Range of the system. The Free Spectral Range is a measure of the wavelength difference between two successive maxima or minima. Typically, a suitable thickness of the optical components is less than 1 mm. This choice presents at worse a Free Spectral Range of 4 $cm^{-1}$ or greater. By controlling the Free Spectral Range, the frequency at which fringing effects occur can be shifted to not coincide and/or interfere with the measurement of the compounds in the sample cell 10.

The Free Spectral Range of this magnitude provides a spectral window that is similar in width to the spectral window covered by an entire laser scan. An expected effect is a curvature on the background of the laser pulse. This background can be easily removed using spectral fitting algorithms as part of the processing the signal. Additional fringing effects are avoided in the steering optical components 22 in the sensor apparatus 12 and optics used to steer light to the sample cell 10 through the use of non-flat or wedged optical components.

Each laser in FIG. 2 has a corresponding mirror belonging to the set of five partially reflective mirrors 32 and one dichroic mirror 34. In operation a laser beam from the first laser 46 passes to the first mirror 36 and then from the first mirror 36 to the point 58. The first mirror 36 is tilted such that the laser beam from the first laser 46 is reflected at a right angle by the first mirror 36. Likewise, each of the second to fifth lasers has a corresponding optical path defined by the second to fifth mirrors. A sixth optical path is defined in the same way from the sixth laser 56 to the dichroic mirror 34 and to the point 58. All of the mirrors are arranged at the same tilted angle as the first mirror 36 such that each of the optical paths bends at a right angle at its point of intersection with its corresponding mirror.

The mirrors are arranged such that laser beams from the lasers 46, 48, 50, 52, 54, 56 pass along a common optical path to the cell 10 via point 58 after reflection by their corresponding optical components 36, 38, 40, 42, 44, 34. The common optical path may, for example, have one end at the first mirror 36 and the other end at the entrance aperture 84 to the sample cell 10 and may extend through point 58 and when directed to pass along the common optical path, the optical paths of each respective laser joins the common optical path. Hence, the optical paths of each laser may substantially overlap.

In operation, the lasers 18 are controlled by the control module 26, or other control component in other embodiments, to sequentially produce pulses. The sequence may be as follows. The first laser 46 produces a first pulse that is directed to point 58 by the optical components and passes onward to the sample cell 10. Subsequently, the second laser 48 produces a second pulse that is directed to point 58 by the optical components and passes onward to the sample cell 10. This is followed, in turn, by a third pulse produced by the third laser 50 that is directed to point 58 by the optical components and passes onward to the sample cell 10, a fourth pulse produced by the fourth laser 52 that is directed to point 58 by the optical components and passes onward to the sample cell 10, a fifth pulse produced by the fifth laser 54 that is directed to point 58 by the optical components and passes onward to the sample cell 10, and a sixth pulse produced by the sixth laser 56 that is directed to point 58 by the optical components and passes onward to the sample cell 10. Following the sixth pulse, this sequence is repeated. The pulsed beams from each of the lasers are interleaved and/or non-overlapping in time and propagate along the common path to the sample cell 10

Following the above sequence, the first pulse is incident on, and reflected by, the first mirror 36 and is then transmitted by the second, third, fourth, fifth and dichroic mirror 34 to point 58 and continues to the sample cell 10 and the detector apparatus 24. Subsequently, the second pulse is incident on, and reflected by, the second mirror 38 and is then transmitted by the third, fourth, fifth and dichroic mirror 34 to point 58 and onward to the sample cell 10 and detector apparatus 24. Subsequently, the third pulse is incident on, and reflected by, the third mirror 40 and then transmitted by the fourth, fifth and dichroic mirror 34 to point 58 and onward to the sample cell 10 and detector apparatus 24. Subsequently, the fourth pulse is incident on, and reflected by, the fourth mirror 42 and is then transmitted by the fifth mirror 44 and the dichroic mirror 34 to point 58 and onward to the sample cell 10 and detector apparatus 24. Subsequently, the fifth pulse is incident on, and reflected by, fifth mirror 44 and is then transmitted by the dichroic mirror 34 to point 58 and onward to the sample cell 10 and detector apparatus 24. The last pulse in the sequence is the sixth pulse and this pulse is incident on and reflected by the dichroic mirror 34 to point 58 and onward to the sample cell 10 and detector apparatus 24. The pulse sequence is then repeated.

The pulses propagate through the sample cell 10 to the sensor apparatus 12. The steering optical components 22 in the sensor apparatus 12 steer light (originating from the first to fifth lasers) from the cell to a first detector that is sensitive to light from the first to fifth lasers. Thus, in this embodiment one of the detectors is sensitive to light from more than one of the lasers. The steering optical components 22 in the sensor apparatus 12 steer light (originating from the sixth laser) from the cell to a second detector that is sensitive to light from the sixth laser 56. The steering optical components 22 include a second dichroic mirror to direct light of the sixth laser 56 towards the second detector and to direct light of the first to fifth lasers to the first detector. The optical properties of the second dichroic mirror may match the properties of the dichroic mirror 34 of the laser module 14. The steering optical components 22 include two separate off-axis parabolic mirrors to focus the two different branches of light onto the two detectors. The control module synchronises operation of the lasers and the first and second detectors, such that each of the detection signals corresponds to light received from a respective one of the lasers.

The lasers 18 of FIG. 1 are semiconductor diode lasers that are operable to produce light over a sub-range of wavelengths. The lasers may be quantum cascade lasers, for example pulsed, chirped quantum cascade lasers, although any other suitable types of laser may be used in alternative embodiments. The lasers may, for example, produce beams of 2 to 3 mm in diameter, or of any other suitable size.

The sub-ranges of wavelengths may be in the infra-red spectrum. The wavelength ranges are chosen to correspond to the measurement of one or more compounds. Together the instrument may provide multiple wavelength ranges of light and combines, for example, visible, near infrared and/or mid infrared light to take advantage of the most suitable wavelengths for each compound. Table 1 shows an example implementation of wavelength ranges for lasers 18, the corresponding wavenumber range and the corresponding compound detected by light in this wavelength range:

TABLE 1

| Laser | Wavelength Range (μm) | Wavenumber Range (cm$^{-1}$) | Compounds Detected |
|---|---|---|---|
| 1 | 5.2632-5.2356 | 1900-1910 | Nitrogen Oxide (NO), Water (H2O) |
| 2 | 6.1538-6.1162 | 1625-1635 | Nitrogen Dioxide (NO2) |
| 3 | 4.4742-4.4743 | 2225-2235 | Carbon Monoxide (CO), Carbon Dioxide (CO2) |
| 4 | 7.4627-7.4349 | 1340-1345 | Methane (CH4), Sulphur Dioxide (SO2) |
| 5 | 10.0-10.2 | 980-1000 | Ammonia (NH3), Acetylene (C2H2) |
| 6 | 0.7605-0.7599 | 13150-13160 | Oxygen (O2) |

Careful selection of wavelength ranges of the lasers allows multiple measurements per laser wavelength. As can be seen in Table 1, the wavelength ranges of the first five lasers are of the same order of magnitude. However, the wavelength range of the sixth laser to detect Oxygen is an order of magnitude smaller. The first and second detectors are selected to detect light in the wavelength ranges of the first to fifth laser, or the wavelength range of the sixth detector respectively.

The control module 26 is configured to send one or more electronic control signals to the lasers 18. In response to the electronic control signals, the lasers 18 produce the combined laser beam 30. The control signal acts to pulse the lasers 18 sequentially. In other words, the control signal acts to drive each of the lasers 18 in a sequence, such that over a sample time interval only light from one laser is provided to the optical components 20. The optical components 20 are configured to direct the light from each laser along the optical path of the laser to follow the common path to the sample cell 10. In this way, the control module 26 controls the laser module 14 to produce the combined laser beam 30 and provide the combined laser beam 30 to the sample cell 10.

The switching frequency between the lasers is selected to ensure a reliable measurement in the sensor apparatus 12. In particular, the time taken for a pulse of light to traverse its sample cell optical path is dependent on the physical properties of the pulse and the dimensions of the sample cell 10. If light from more than one laser is incident in the sample cell 10 over a sample time interval then interference can occur leading to an unreliable measurement. Therefore, the pulse lengths and frequency of subsequent laser pulses are controlled and selected to take into account the time taken by light to traverse its sample cell optical path to ensure that light from only one laser is present inside the sample cell 10 over a sample time interval. Suitable pulse durations for pulses from the lasers 18 may be between 100 nanoseconds and 5000 nanoseconds. The frequency of sequential pulsing may be up to 100 kHz in some embodiments.

The signal processor 28 processes the detection signals from the detectors to determine the concentrations and/or relative amounts of the different compounds under investigation, or to determine any other desired properties. The signal processor 28 uses any suitable known processing techniques to determine the concentrations, relative amounts or other properties.

A calibration mechanism may also be provided. An example calibration mechanism comprises a camera and a mirror adjustment mechanism. The camera or is positioned at or near the point 58 to intersect a desired direction of propagation of the combined laser beam 30. The desired direction of propagation is such that the combined laser beam 30 will, in normal operation, enter the sample cell 10 via the common optical path. During a calibration step, sample beams are produced by the lasers 18 and the sample beams are directed by the optical components 20 to the camera. The camera detects the position of the sample beams incident on it relative to the desired direction of propagation. The mirror adjustment mechanism adjusts the position, in particular the tilt relative to the direction of propagation, of the partially reflective mirrors 32 and dichroic mirror 34 to substantially align the optical paths of the lasers 18 with the desired direction of propagation and substantially align the optical paths with each other. For example, the optical paths are substantially aligned within a 1.1° tolerance. The calibration step is repeated for each of the lasers 18.

Figure 3:
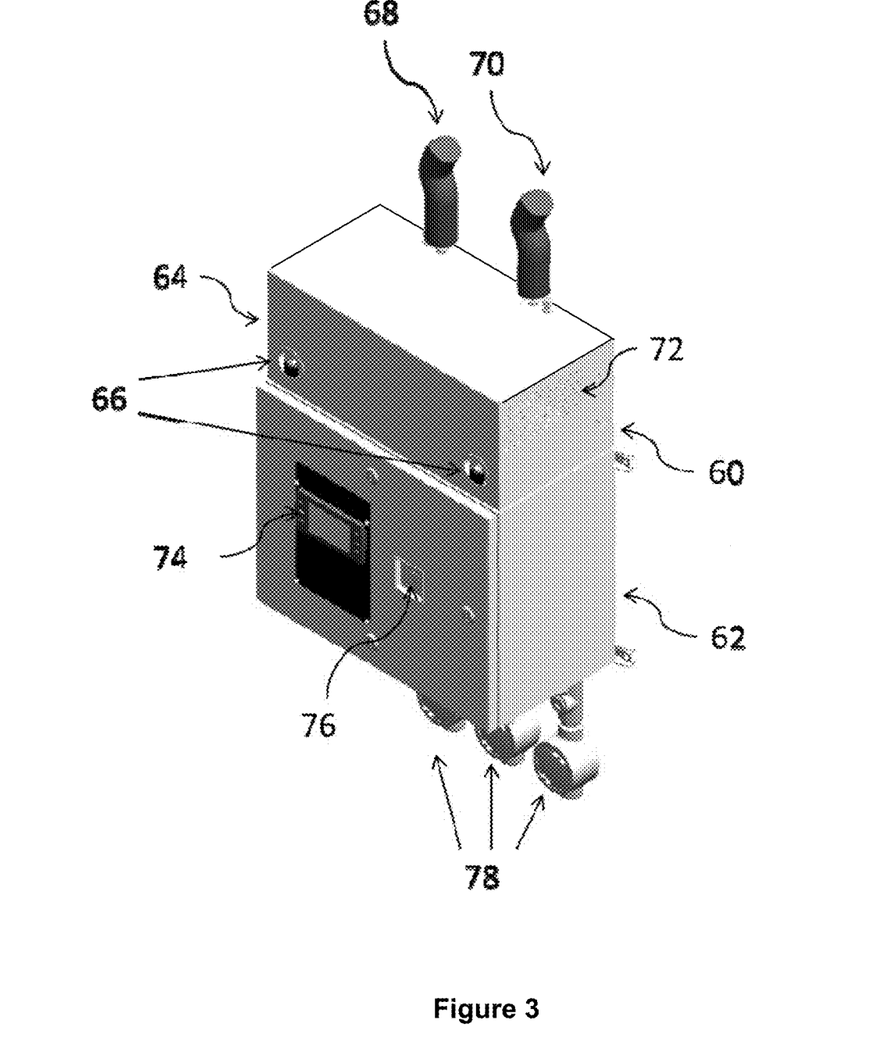
FIG. 3 is a perspective view of housing for the laser spectroscopy system.

FIG. 3 is a perspective view of housing for the laser spectroscopy system. The housing has an upper section 60 and a lower section 62. The upper section 60 has a lift-off cover 64 that is secured in a closed position by a first and second release catch 66. The sample cell 10 is located in the upper section 60 of the housing. A gas supply arrangement in the form of sample supply tube 68 provides gas to the sample cell. A sample return tube 70 provides an outlet for gas from the sample cell. Ventilation is provided to the sample cell via a vent 72 in the upper section 60. The lower section 62 has a local operator user input display 74 and a purge control display 76. In the embodiment of FIG. 3, the user input display is for interaction with the analyser and visual communication of measurements and status. Some maintenance functionality is provided by the user input display in this embodiment, however its purpose is mostly communication of measurement values and status.

The purge control display 76 of the embodiment of FIG. 3 is used control the air purge of the enclosure. This can be a requirement of hazardous area installations where steps must be taken to prevent fire hazards. In this case an air purge controlled via the purge control display 76 supplies, for example constantly supplies, the enclosure or housing of the system with clean air to prevent an explosive environment from building up.

Also connected to the lower section 62 are three output conduits 78. The conduits provide electrical breakthroughs that allow power and control signals to be sent to the system and to allow data to be transmitted from the system. The data transmitted may, for example, be in the form of digital signals, digital health signals, analogue signals for example 4-20 mA signals indicating measured values of gases, more sophisticated protocols such as Modbus, or in any other suitable format. The arrangement described above provides a compact system. In some embodiments, the housing may be around 550 cm long, the upper section may be around 200 cm tall and the lower section may be around 370 cm tall.

The sample supply tube 68 and the sample return tube 70 provides a fluid communication path through the sample cell. The sample gas can be collected from a remote location and can be delivered via the sample supply tube 68 to the sample cell to be sampled. The sample gas can then be exhausted from the sample cell via the sample return tube 70. Together, the sample supply tube 68 and the sample return tube 70 allow for the instrument to operate remotely, in contrast to in-situ emission sensing. Any other suitable gas supply arrangement may be used in alternative embodiments.

A sample handling system (SHS) unit (not shown) may be provided to control pressure of the gas in the sample cell 10. Any suitable SHS unit or other pressure control device may be used, which may or may not comprise or be driven by a pump and may or may not comprise other pressure control components such as an arrangement of valves. In the embodiment of FIG. 3, the SHS unit includes an aspirator rather than a pump, although a pump or other pressure control device or components may be used in other embodiments.

Additionally, the housing contains at least one absorber component to absorb laser light that is not directed along the common path to the sample cell 10. The at least one absorber component may contain additional optical components, for example wedged optical components.

Figure 4:
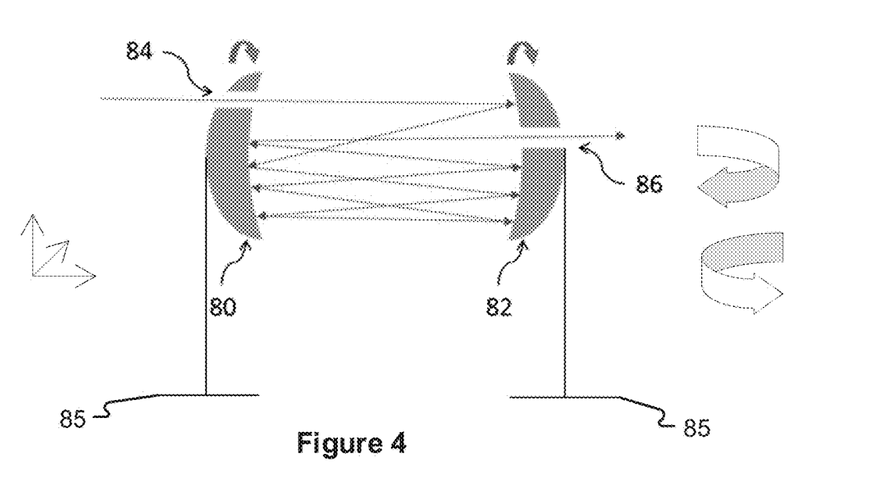
FIG. 4 is a schematic view of a multi-pass optical cell.

FIG. 4 show the sample cell 10 of the embodiment of FIG. 1 in more detail. The cell comprises a first reflecting element 80, a second reflecting element 82, an entrance aperture 84 and an exit aperture 86. The entrance aperture 84 has a diameter large enough to permit entry of the laser beam. For example, the laser beam may have a diameter of 2 to 3 mm. The reflecting elements may be paraboloid mirrors. The first reflecting element 80 and second reflecting element 82 oppose each other and are separated by a lateral length. A central axis extends between a central point of the first reflecting element 80 and a central point of the second reflecting element 82 along the lateral length. The entrance aperture 84 is positioned on the first reflecting element 80 and the exit aperture 86 is positioned on the second reflecting element 82. This placement is in contrast to a standard Herriott cell where only one aperture, providing an entrance and an exit, is provided on one reflecting element. The sample cell of FIG. 4 allows input optics and output optics to be spatially separately positioned on opposing sides of the cell. Advantageously, this may reduce the overall volume of the system and may improve ease of access from maintenance and production. The separation or lasers on one side of the cell and detectors on the other side may provide a simplified arrangement, and may require less complex arrangements of steering optics or other components within the housing of the system.

The exit aperture 86 is positioned such that light introduced into the cell through the entrance aperture 84 does not proceed directly to the exit aperture 86 but instead is reflected at least once off the second reflecting element 82 before reaching the exit aperture 86. Light reflected off the second reflecting element 82 will be reflected off the first reflecting element 80 at least once before reaching the exit aperture 86. The position of the exit aperture 86 therefore defines the number of reflections between the first and second reflecting element taken by the light before exiting the cell and hence the path length of light in the cell.

The sample cell has an adjustment mechanism 85 to move the second reflecting element 82 relative to the first reflecting element 80 (or vice versa) and hence move the exit aperture 86 relative to the entrance aperture 84 thereby modifying the sample cell path length. In one embodiment, the adjustment mechanism 85 comprises a translation mechanism configured to translate the second reflecting element 82 relative to the first reflecting element 80 in the direction of the central axis. By translating the second reflecting element 82, the path length of the optical path in the cell can be changed, as the number of reflections is dependent on the lateral length between the two opposing reflecting elements.

A second embodiment of the adjustment mechanism 85 comprises a rotation mechanism configured to rotate the second reflecting element 82 relative to the first reflecting element 80. The rotation is about the central axis. Rotation of the second reflecting element 82 modifies the position of the exit aperture 86 relative to the central point of the second reflecting element 82. The path length of the optical path in the sample cell can be easily modified in discrete distance intervals by rotating the second reflecting element 82. For example, the path length can be changed in steps of 40 cm up to a total of 5 meters. The adjustment mechanism 85 in either the first or second embodiments mentioned may comprise any suitable combination or mechanical components and/or electrical components and/or electro-mechanical components and/or one or more actuators.

Figure 5:
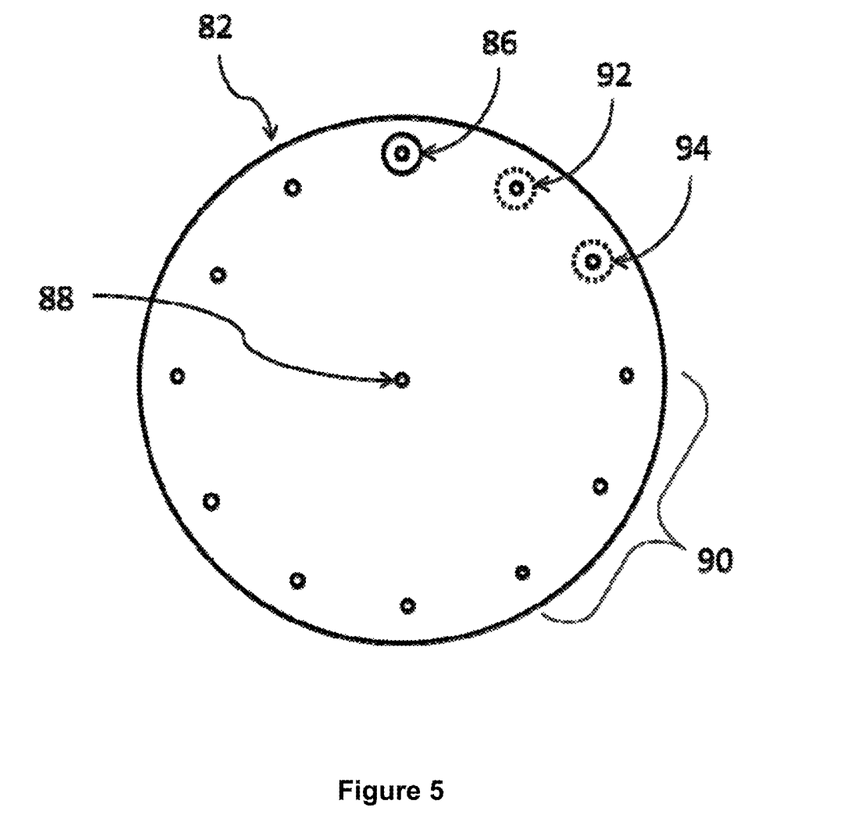
FIG. 5 is a schematic view of a reflecting element of the multi-pass optical cell.

FIG. 5 is a view of the second reflecting element 82 of the second embodiment of the sample cell. FIG. 5 shows an internal surface of the second reflecting element 82 as viewed along the central axis of the sample cell. The central axis runs through a centre point 88 of the second reflecting element 82. As can be seen, the second reflecting element 82 has a rotational symmetry about the central axis. Around the periphery of the second reflecting element 82 is a plurality of reflection points 90. In FIG. 5, the second reflecting element 82, as viewed along the central axis, is circular and has 12 reflection points. Each reflection point in this embodiment is at substantially the same radial distance from the centre point 88, although any suitable alternative arrangement of reflection points can be provided in alternative embodiments. An angle of 30 degrees at centre point 88 separates each subsequent reflection point in the embodiment of FIG. 5.

Also indicated on FIG. 5 is the exit aperture 86 of the second reflecting element 82 at an aperture radius from the centre point 88. FIG. 5 also shows two alternative shifted positions for the exit aperture 86: a first shifted position 92 and a second shifted position 94. The first shifted position 92 is at an angle of 30 degrees from the position of the exit aperture 86 and the second shifted position 94 is at an angle of 60 degrees from position of the exit aperture 86. Although only two alternative shifted positions are shown, each of the plurality of reflection points 90 offers a possible shifted position for the exit aperture 86, as described below.

In operation, light introduced into the sample cell via the entrance aperture 84 of the first reflecting element 80 is incident on the second reflecting element 82 at a first reflection point of the plurality of reflection points 90 and reflects off the second reflecting element 82 at said first reflecting point. The reflected light travels back to and is thereby incident on the first reflecting element 80, where it is again reflected and returned to the second reflecting element 82. The transit of light from the first reflecting element 80 to the second reflecting element 82 and back to the first reflecting element 80 defines a single pass of light in the sample cell. Generally, light introduced into the sample cell will perform more than one pass before exiting through the exit aperture 86 of the second reflecting element 82. Each subsequent pass will visit a different reflection point of the plurality of reflection points 90 on the second reflecting element 82.

The sample cell therefore has an intrinsic radiation pattern defined by the physical properties of the reflecting elements and the physical dimensions of the cell. Other radiation patterns can be produced and hence other arrangement and/or numbers of reflection points can be created by changing the physical properties of the sample cell, for example, by changing the physical dimensions of the reflecting element or the lateral length between the reflecting elements. A radiation path between the entrance aperture 84 and the exit aperture 86 can be characterised by the subset of the reflection points 90 that the light visits on transit between the apertures. The position of the exit aperture 86 over one of the reflection points therefore defines the radiation path. Each additional pass of light will add a distance to the total sample cell path length. For example shown, the distance light travels between the first and second reflecting element is 20 cm and hence the pass distance is 40 cm.

As described above, the second embodiment of the adjustment mechanism comprises a rotation mechanism configured to rotate the second reflecting element 82 relative to the first reflecting element 80. This rotation causes rotation of the exit aperture 86. The second reflecting element 82 can be rotated such that the exit aperture 86 overlies any of the plurality of reflection points 90. As a non-limiting example, the exit aperture 86 can be at the first shifted position 92 or the second shifted position 94. A radiation path between the entrance aperture 84 and the exit aperture at the first shifted position 92 will comprise an additional pass length relative to a radiation path between the entrance aperture 84 and the exit aperture at the first shifted position 92. Therefore, the rotation mechanism can set the radiation path and hence path length for light introduced into the sample cell.

The embodiments of the sample cell described with respect to FIG. 4 and FIG. 5 are not limited to use within a multiple laser setup. The sample cell can also be used in different optical configurations. For example, the sample cell can be used with a single laser or other radiation source, instead of the multi-laser arrangement of FIGS. 1 and 2. In such a setup, the single radiation source is arranged such that radiation produced by the source enters the entrance aperture 84 of the cell and exits through the exit aperture 86. In some alternative embodiments the laser module 14 of the system of FIG. 1 is replaced with a laser module or other laser source that has a single laser for providing the laser beam to the cell 10 rather than multiple lasers. Other components may be substantially the same as the components of the system of FIG. 1 in some such alternative embodiments. Additional optical components may be provided in some embodiments to steer the light into and out of the sample cell and/or towards a photodetector.

A skilled person will appreciate that variations of the described embodiments are possible without departing from the scope of the claimed invention. For example, while it is discussed that a control module in the controller is used to sequentially pulse the output of the lasers allowing the combined beam to be produced, other controller arrangements can also be used. One alternative is a mechanical optical switching arrangement that physically controls laser light such that only one laser provides light to the optical components over a given interval of time. As another example, the lasers described are semiconductor diode lasers that operate over a wavelength range. However, the lasers may be any suitable radiation source capable of providing suitable wavelengths of light. Additionally, the lasers may be single wavelength. Another example, of a modification is to replace the off-axis parabolic mirrors with any suitable focussing arrangement. Accordingly, the above description of the specific embodiments is made by way of example only and not for the purposes of limitations. It will be clear to the skilled person that minor modifications may be made without significant changes to the operations described.

The invention claimed is:

1. An optical cell comprising:
    first and second opposed reflecting elements;
    an entrance aperture in the first reflecting element;
    an exit aperture in the second reflecting element, wherein the entrance and exit apertures are configured such that, in operation, light introduced into the optical cell via the entrance aperture is reflected at least once by the second reflecting element and at least once by the first reflecting element before leaving the optical cell via the exit aperture, and wherein in operation said light reflects from the first reflective element at a plurality of first reflection points and reflects from the second reflective element at a plurality of second reflection points; and
    an adjustment apparatus for obtaining relative rotational movement of the second reflecting element and the first reflecting element thereby to position the exit aperture at a selected one of the plurality of second reflection points,
    wherein a path followed by the light between the entrance and exit apertures defines a path length, and
    wherein the adjustment apparatus obtains the relative rotational movement of the second reflecting element and the first reflecting element such that the path length of the optical cell is modified.

2. An optical cell according to claim 1, wherein the optical cell comprises a Herriot-type cell.

3. An optical cell according to claim 1, wherein the adjustment apparatus is configured to modify the path length by modifying the number of reflections of the light between entering the optical cell and exiting the optical cell.

4. An optical cell according to claim 1, wherein the relative rotational movement comprises a rotation of the second reflecting element and/or the first reflecting element.

5. An optical cell according to claim 1, wherein the relative rotational movement comprises a translation of the second reflecting element and/or the first reflecting element.

6. An optical cell according to claim 1, wherein the adjustment apparatus is configured to obtain said relative rotational movement such as to step the position of the exit aperture from the selected one of the second reflection points to a further, selected one of the second reflection points.

7. An optical cell according to claim 1, wherein at least one of:
the plurality of first reflection points are each arranged at substantially the same radial distance from an axis of the first reflecting element; and
the plurality of second reflection points are each arranged at substantially the same radial distance from an axis of the second reflecting element.

8. An optical cell according to claim 1, wherein at least one of:
each of the plurality of first reflection points is spaced from a respective neighbouring one of the plurality of first reflection points by substantially the same first angle; and
each of the plurality of first reflection points is spaced from a respective neighbouring one of the plurality of second reflection points by substantially the same second angle.

9. An optical cell according to claim 1, wherein at least one of:
the entrance aperture is located at an off-axis position with respect to a central axis of the first reflecting element; and
the exit aperture is located at an off-axis position with respect to a central axis of the second reflecting element.

10. An optical cell according to claim 1, wherein at least one of:
the first reflecting element has a reflecting surface that is circularly symmetric; and
the second reflecting element has a reflecting surface that is circularly symmetric.

11. An optical cell according to claim 1, wherein at least one of:
the first reflecting element comprises a paraboloid mirror; and
the second reflecting element comprises a paraboloid mirror.

12. A detection system comprising:
at least one laser configured to produce at least one laser beam for excitation of one or more different compounds;
a sample cell for containing a volume of sample gas;
at least one directing device configured to direct the at least one laser beam to the sample cell;
a detector apparatus for detecting light output from the sample cell, wherein
the sample cell comprises:
first and second opposed reflecting elements;
an entrance aperture in the first reflecting; and
an exit aperture in the second reflecting element, wherein the entrance and exit apertures are configured such that, in operation, light introduced into the sample cell via the entrance aperture is reflected at least once by the second reflecting element and at least once by the first reflecting element before leaving the sample cell via the exit aperture, and wherein in operation said light reflects from the first reflective element at a plurality of first reflection points and reflects from the second reflective element at a plurality of second reflection points; and
an adjustment apparatus for obtaining relative rotational movement of the second reflecting element and the first reflecting element thereby to position the exit aperture at a selected one of the plurality of second reflection points,
wherein a path followed by the light between the entrance and exit apertures defines a path length, and
wherein the adjustment apparatus obtains the relative rotational movement of the second reflecting element and the first reflecting element such that the path length of the sample cell is modified.

13. A detection system according to claim 12, wherein the detector apparatus is arranged at a first side of the sample cell and the at least one laser is arranged at a second, substantially opposite side of the sample cell.

14. A detection system according to claim 12, wherein the system is a continuous emission monitoring system.

15. A detection system according to claim 12, wherein the at least one compound comprises at least one of: $NO$, $NO_2$, $H_2O$, $CO$, $CO_2$, $CH_4$, $SO_2$, $NH_3$, $C_2H_2$ and $O_2$.

16. A method of testing, measuring or detecting the presence of a gas comprising:
directing light into a sample cell containing the gas via an entrance aperture in a first reflecting element of the sample cell;
reflecting the light from the first reflective element at a plurality of first reflection points and reflecting the light from a second reflective element at a plurality of second reflection points;
receiving the light from an exit aperture in the second reflecting element of the sample cell following reflection of the light between the first and second reflecting elements; and
detecting the received light, wherein the method further comprises:
performing a relative rotational movement of the second reflecting element and the first reflecting element thereby to position the exit aperture at a selected one of the plurality of second reflection points,
wherein a path followed by the light between the entrance and exit apertures defines a path length, and
wherein the performing the relative rotational movement obtains the relative rotational movement of the second reflecting element and the first reflecting element such that the path length of the sample cell is modified.

* * * * *